United States Patent [19]

Wu

[11] Patent Number: 5,632,882

[45] Date of Patent: May 27, 1997

[54] ELECTROLYTES FOR INHIBITING SILVER DEPOSITION ON OXYGEN SENSOR CATHODES AND METHODS OF USE OF SAME

[75] Inventor: Huan P. Wu, Beavercreek, Ohio

[73] Assignee: YSI Incorporated, Yellow Springs, Ohio

[21] Appl. No.: 681,657

[22] Filed: Jul. 29, 1996

[51] Int. Cl.$^6$ .................................................. G01N 27/404
[52] U.S. Cl. ...................... 205/783; 204/402; 204/415; 204/435; 205/782; 205/782.5
[58] Field of Search .................................. 204/402, 415, 204/435; 205/782, 782.5, 783; 429/199, 203, 204, 205

[56] References Cited

U.S. PATENT DOCUMENTS

| | | | |
|---|---|---|---|
| 2,913,386 | 11/1959 | Clark | 204/415 |
| 3,380,905 | 4/1968 | Clark, Jr. | 204/195 |
| 3,406,109 | 10/1968 | Molloy | 204/415 |
| 3,701,684 | 10/1972 | De Rossi | 429/199 |
| 4,018,660 | 4/1977 | Hansen et al. | 204/195 |
| 4,074,028 | 2/1978 | Will | 429/199 |
| 4,245,015 | 1/1981 | Burke | 429/199 |
| 4,729,824 | 3/1988 | Giner | 204/415 |
| 4,803,991 | 2/1989 | Alena et al. | 128/635 |
| 4,824,551 | 4/1989 | Rupich | 204/415 |
| 4,853,091 | 8/1989 | Mund et al. | 204/204 |
| 5,215,644 | 6/1993 | Ashikaga | 204/412 |
| 5,217,595 | 6/1993 | Smith et al. | 204/412 |
| 5,254,235 | 10/1993 | Wu | 204/284 |
| 5,358,619 | 10/1994 | Suzuki et al. | 204/403 |
| 5,423,963 | 6/1995 | Fletcher et al. | 204/153.17 |

OTHER PUBLICATIONS

Quantitive Chemical Analysis, pp. 133–134, Kolthoff, I.M., et al.; 4th Edition, The MacMillan Co., New York 1968 month unavailable.

*Primary Examiner*—T. Tung
*Attorney, Agent, or Firm*—Biebel & French

[57] ABSTRACT

A Clark-type gas detection apparatus includes a sensor electrode and a reference electrode exposed to an aqueous electrolyte solution which is isolated from a liquid medium surrounding the apparatus by a semi-permeable membrane. A preferred reference electrode for use in Clark-type apparatus comprises silver/silver chloride. Through the addition of an effective amount of a sulphate-based co-electrolyte to an electrolyte solution having a relatively low chloride ion content, it is possible to obtain an electrolyte solution having an ionic conductivity comparable to that of chloride-based electrolyte solutions currently used in Clark-type sensors while retaining sufficient chloride ion to drive the oxidation reaction near the reference electrode. The relatively low chloride ion content of the electrolyte solution of the present invention tends to suppress the dissolution of silver chloride from the reference electrode, and, consequently, the deposition of silver on the indicating electrode.

21 Claims, 6 Drawing Sheets

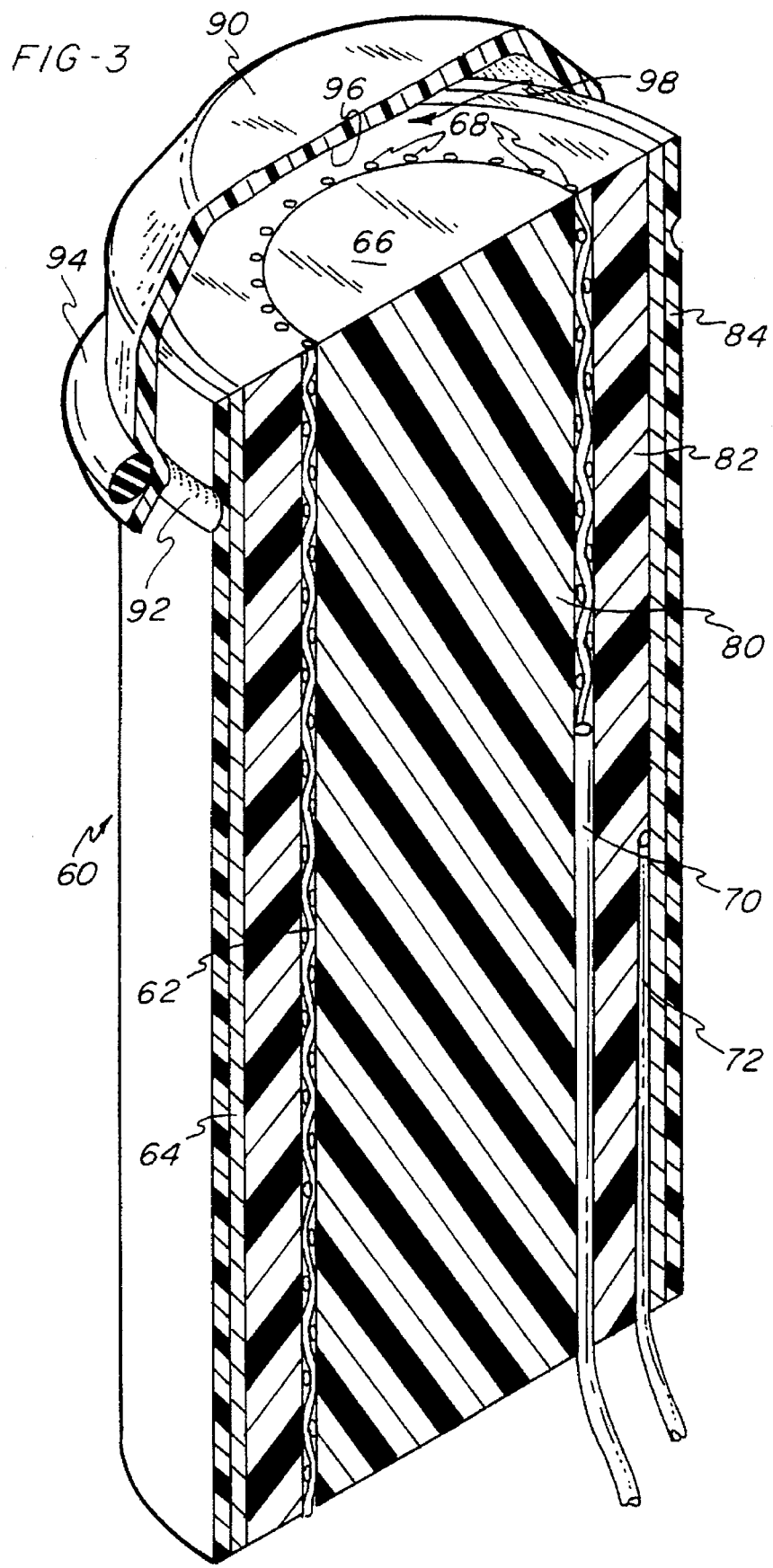

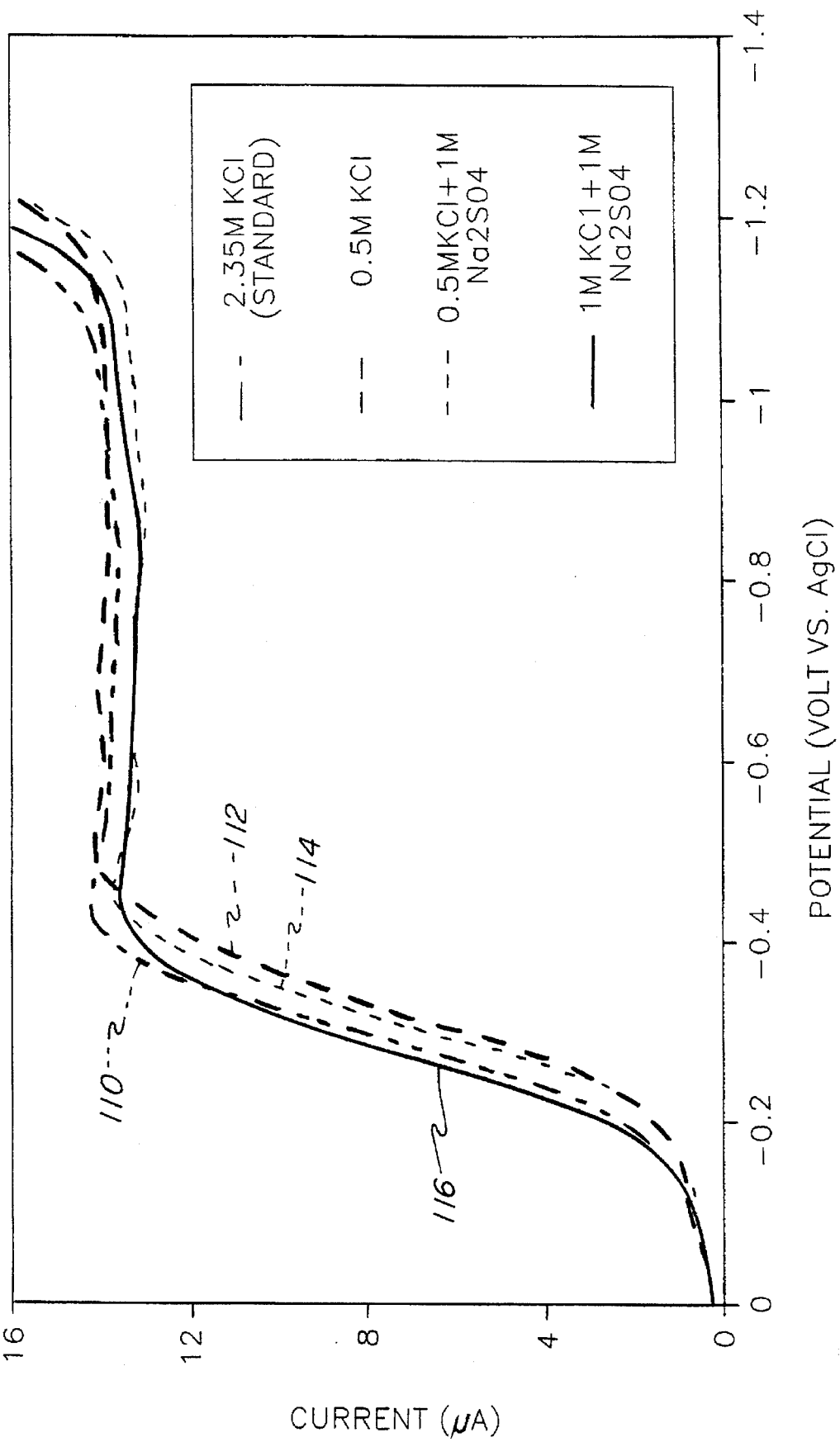

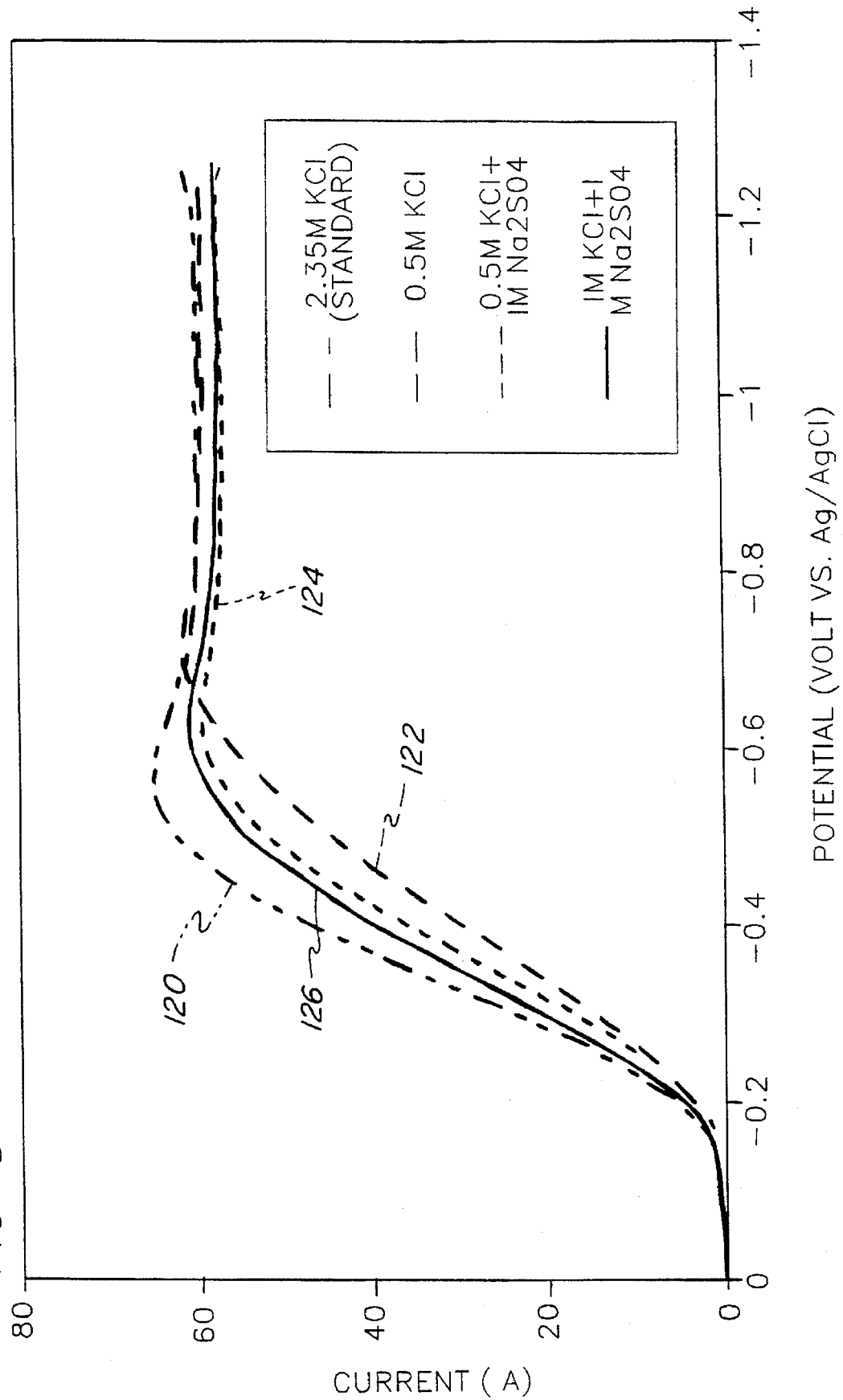

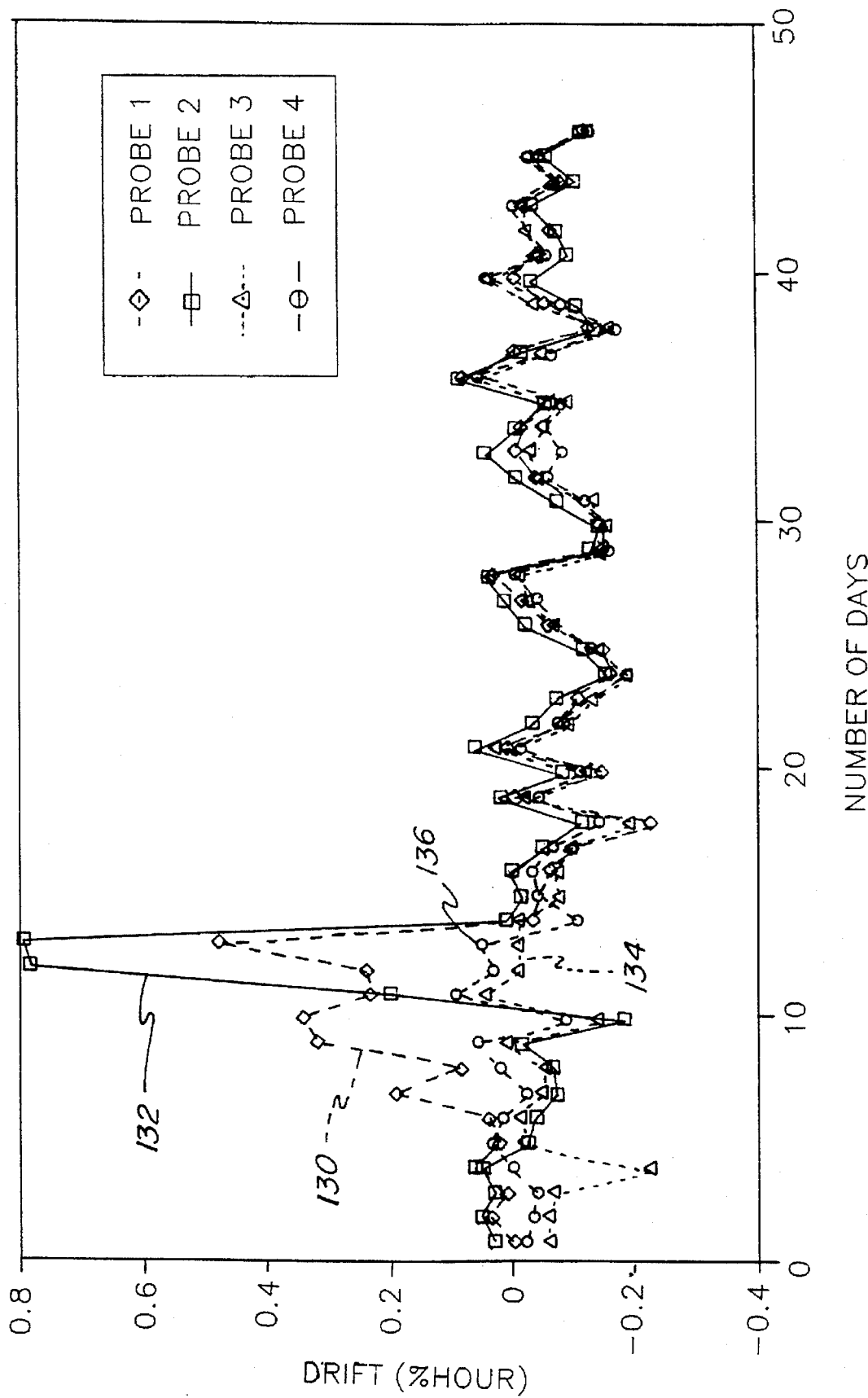

ELECTROLYTES FOR INHIBITING SILVER DEPOSITION ON OXYGEN SENSOR CATHODES AND METHODS OF USE OF SAME

BACKGROUND OF THE INVENTION

1. Field of the Invention

This invention relates to the field of oxygen gas detection, and more particularly relates to electrolyte-formulations and methods of using those formulations to inhibit undesired deposit formation on cathodes used in the detection equipment. More specifically, the electrolytes and method suppress the dissolution of silver chloride from silver/silver chloride reference electrodes and the attendant deposition of silver on neighboring electrodes.

2. Description of the Related Art

Polarographic sensors of the type disclosed in Clark U.S. Pat. No. 2,913,386 have become increasingly popular in medical, biological, industrial and environmental applications for detecting and measuring gases such as oxygen dissolved in a liquid medium. A Clark-type sensor includes a sensor electrode and a reference electrode exposed to an aqueous electrolyte solution which is isolated from the liquid medium by a semi-permeable membrane. In the specific case of a dissolved oxygen sensor, oxygen diffuses from the liquid medium through the semi-permeable membrane into the electrolyte solution at a rate proportional to the oxygen partial pressure in the liquid medium. The diffused oxygen migrates toward the sensor electrode (which is configured as a cathode) where it is reduced in accordance with the following reaction:

$$O_2 + 4H^+ + 4e^- \rightarrow 2H_2O \qquad (I)$$

This reaction induces an electron flow from the sensor electrode having a current magnitude proportional to the oxygen partial pressure in the liquid medium.

Silver/silver chloride electrodes are commonly used as a reference electrode in such Clark sensors due to the stability of its oxidation potential over a wide temperature range in a chloride-based electrolyte solution. The oxidation potential of a silver/silver chloride electrode is established by the reaction:

$$Ag + Cl^- \rightarrow AgCl + e^-. \qquad (II)$$

Chloride-based electrolyte solutions perform two functions in a polarographic sensor having a silver/silver chloride electrode. They supply ions in the electrolyte solution to conduct the current necessary to maintain the reactions at the sensor and reference electrodes, and they supply the Cl ions to this anode/reference electrode for the oxidation of Ag in accordance with the preceeding oxidation of Ag (II). Over time, the reaction near the reference electrodes exhausts the chloride ion concentration, so that the electrolyte solution must be replaced periodically to maintain the accuracy of the sensor.

One drawback to the use of silver/silver chloride reference electrodes in a chloride-based electrolyte solution is the plating or formation of Ag onto the sensor or cathode electrode. The solubility of silver chloride in an aqueous solution increases with increasing chloride ion concentration in the solution. Silver chloride is practically insoluble in pure water, having a solubility product constant of approximately $1 \times 10^{-10}$. On the other hand, AgCl readily dissolves into a high chloride medium to form $Ag(Cl_2)^-$. The total solubility of silver chloride in the forms of $Ag^+$, AgCl and $Ag(Cl_2)^-$ is plotted as a function of the logarithm of chloride ion concentration in FIG. 1. As shown by the curve 10 in FIG. 1, the total solubility of silver chloride increases rapidly above a chloride ion concentration of approximately $1 \times 10^{-2}$M.

Thus, a common problem with Clark-type sensors using silver/silver chloride reference electrodes and chloride-based electrolyte solutions is the dissolution of silver chloride from the reference electrode and the deposition of silver in the form of dendrites on the sensor electrode. Dendrite formation at the cathode of an oxygen sensor has resulted in the following two symptoms: (1) the oxygen reading gradually rises with time at a rate of about 0.5–1% per hour and (2) the oxygen reading fluctuates frequently and drastically. These two symptoms can be explained by the deposition of silver in the following way: the addition of silver to the cathode increases the area of the cathode which in turn increases the sensor current. Additionally, when dendrites grow large enough in size, some of them break off from the cathode which causes the reading to drop. Then, these broken off dendrites sometimes attach themselves back to the dendrites at the cathode, causing a sudden rise in the oxygen reading.

Various techniques have been proposed to suppress the deposition of silver on the sensor electrodes of Clark-type sensors. For example, Molloy U.S. Pat. No. 3,406,109 proposed placing a moat or groove between the sensor electrode and the reference electrode to interrupt the migration of silver ions toward the sensor electrode. While the placement of a moat between the electrodes as shown in Molloy does reduce the level of silver deposition in certain sensor geometries, the moat does not completely prevent such deposition. Furthermore, space limitations preclude the placement of such moats in a large number of commercially available sensor configurations.

Clark U.S. Pat. No. 3,380,905 and Alena et al. U.S. Pat. No. 4,803,991 each proposed using a quinhydrone reference electrode rather than a silver/silver chloride electrode by adding a small amount of hydroquinone to the electrolyte solution. While such proposals are effective in inhibiting silver deposition on the sensor electrode, they complicate the structure of the sensor and would require that existing sensors using silver/silver chloride reference electrodes be redesigned to accommodate different current levels. Thus, there remains a need for a solution to the problem of silver deposition on the cathodes of Clark-type sensors which is compatible with existing sensor configurations using silver/silver chloride reference electrodes.

SUMMARY OF THE INVENTION

This need is addressed by a Clark-type sensor such as the one shown in U.S. Pat. No. 2,913,386, incorporated by reference herein, using a silver/silver chloride reference electrode and an aqueous electrolyte solution including approximately 1 mM to 1.5M of a chloride salt and approximately 10 mM to 2M of a sulphate salt. Aqueous solutions of sulphate salts like sodium sulphate are excellent ionic conductors of electricity—in fact, the higher valence of $SO_4^{2-}$ ions makes sulphate salts more efficient ionic conductors of electricity per mole than chloride salts such as potassium chloride or sodium chloride. Through the addition of an effective amount of a sulphate-based co-electrolyte to an electrolyte solution having a relatively low chloride ion content, it is possible to obtain an electrolyte solution having an ionic conductivity comparable to that of chloride-based electrolyte solutions currently used in Clark-type sensors while retaining sufficient chloride ion to supply the oxidation reaction at the reference electrode. The relatively low chloride ion content of the electrolyte solution of the present invention tends to suppress the dissolution of silver chloride from the reference electrode, and, consequently, the severe accumulation of silver on the sensor electrode.

In particular, a preferred form of the invention includes an apparatus for detecting a gas dissolved in a liquid medium. The apparatus comprises an aqueous electrolyte solution; an enclosure defining a cavity for containing the aqueous electrolyte solution, the enclosure being permeable to the gas and substantially impermeable to the liquid medium; and a plurality of spaced electrodes in electrical communication with the aqueous electrolyte solution. In an especially preferred form, the enclosure includes a rigid casing substantially impermeable to the gas and a membrane permeable to the gas, the membrane being affixed to the casing by means of an elastic ring and bounding at least a portion of the cavity. A reference electrode among the plurality of spaced electrodes includes a material selected from the group consisting of silver, silver chloride and alloys thereof, and is most preferably a standard silver/silver chloride reference electrode. The aqueous electrolyte solution includes approximately 1 mM to 1.5M of a chloride salt and 10 mM to 2M of a sulphate salt. Preferred chloride salts include potassium chloride and sodium chloride, while preferred sulphate salts include potassium sulphate and sodium sulphate.

Since the current levels in the sensor depend, at least in part, on the electrode geometries, different concentrations of chloride and sulphate salts in the electrolyte solution are preferred for different electrode geometries. A first embodiment of a Clark-type sensor includes a single sensor macroelectrode surrounded by a cylindrical sleeve-like reference electrode. Such an arrangement requires a relatively high current level, and the preferred composition for an electrolyte solution for use in this embodiment includes approximately 0.1M to 1.5M of the chloride salt and 0.1M to 2M of the sulphate salt.

A second embodiment of a Clark-type sensor includes a minigrid defining a circular array of microelectrodes surrounded by a cylindrical sleeve-like reference electrode. A gas detection apparatus including a minigrid defining an indicating microelectrode array is described in more detail in U.S. Pat. No. 5,254,235, the disclosure of which is incorporated herein by reference. Such an arrangement operates at a lower current level than does an arrangement including a single indicating macroelectrode, and the preferred composition for an electrolyte solution for use with this embodiment includes approximately 1 mM to 100 mM of the chloride salt and approximately 10 mM to 200 mM of the sulphate salt.

A significant advantage to the use of a sulphate-based co-electrolyte is the relative inertness of the sulphate ion to other species present in a Clark-type sensor. While other cationic species have sufficient electronegativity to act as co-electrolytes in a chloride solution, many such cationic species, such as nitrates or perchlorates, produce unwanted precipitates or reactions which interfere with the functioning of the sensor.

Therefore, it is one object of the invention to provide a Clark-type sensor including an electrolyte solution having a low chloride ion concentration which suppresses the deposition of silver from a silver/silver chloride reference electrode onto the sensor electrode. Preferably, this is accomplished by means of a Clark-type sensor using an electrolyte solution combining the low chloride ion concentration with a co-electrolyte. The invention will be further described in conjunction with the appended drawings and following detailed description.

BRIEF DESCRIPTION OF THE DRAWINGS

FIG. 3 is a schematic view showing a second embodiment of a gas detection apparatus according to the present invention, partially broken away to show the electrodes and the electrolyte solution;

FIG. 4 is a diagram showing current flow between sensor and reference electrodes of four polarographic oxygen sensors of the type shown in FIG. 2 using different electrolyte solutions as functions of applied voltage, when exposed to air (21% $O_2$);

FIG. 5 is a diagram showing current flow between the sensor and reference electrodes of the four polarographic oxygen sensors as functions of applied voltage, when exposed to pure oxygen gas; and FIG. 6 is a diagram showing daily percentage current drifts for four polarographic oxygen sensors, two of which used chloride-based electrolyte solutions and two of which used electrolyte solutions in accordance with the present invention.

DETAILED DESCRIPTION OF THE PREFERRED EMBODIMENT

Figure 2:
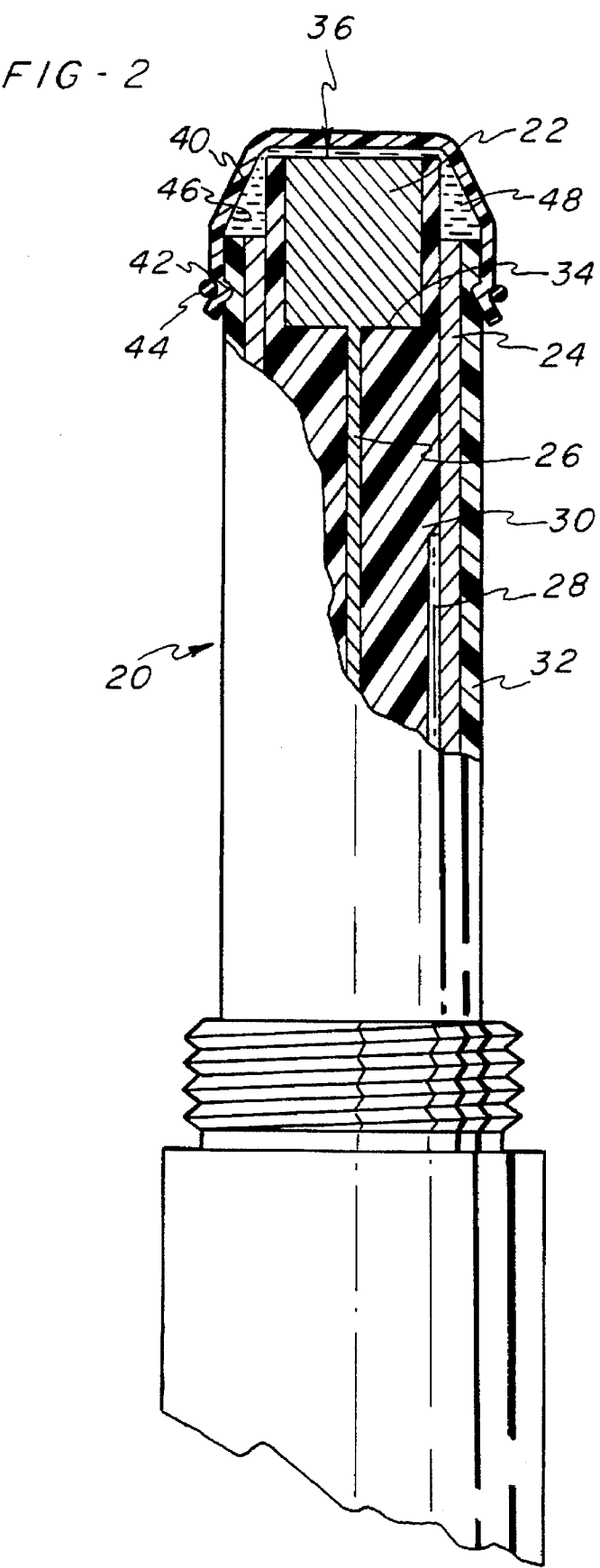
FIG. 2 is a schematic view showing a first embodiment of a gas detection apparatus according to the present invention, partially broken away to show electrodes and an electrolyte solution.

FIG. 2 is a schematic view of a first embodiment 20 of a gas detection apparatus capable of use as a polarographic dissolved oxygen sensor. The apparatus 20 includes a sensor electrode or macroelectrode 22, having a diameter on the order of 5 mm, surrounded by a reference electrode 24. The sensor electrode 22 preferably consists of a gold or platinum disc, and the reference electrode 24 preferably consists of a cylindrical silver/silver chloride sleeve. A first lead 26 communicates with the sensor electrode 22 and a second lead 28 communicates with the reference electrode 24. The first and second leads 26, 28 cooperate to form a coupling for use in generating a current flow between the source and reference electrodes 22, 24 and for conducting signals from the source and reference electrodes 22, 24 to monitoring circuitry (not shown).

The sensor and reference electrodes 22, 24 are separated by an electrically insulating epoxy spacer 30 and the reference electrode 24 is surrounded by a cylindrical epoxy casing or sleeve 32 which electrically isolates the reference electrode 24 from a surrounding liquid medium (not shown). The spacer 30 includes a central passageway having a shoulder 34 for positioning the indicating electrode 22 near a working end 36 of the apparatus 20 and a narrow passageway extending proximally from the shoulder to accommodate the first electrode 26.

A membrane 40 preferably a Teflon® construction, covers the working end 36 of the apparatus 20 and is secured along its periphery in a groove 42 in the casing 32 by means of an elastic ring 44. The casing 32 and the membrane 40 together act as an enclosure for the sensor and reference electrodes 22, 24, respectively defining a cavity 46 to which the electrodes 22, 24 are exposed. An electrolyte solution 48 is enclosed in the cavity 46 in contact with the indicating and reference electrodes 22, 24. The membrane 40 is preferably semi-permeable in the sense that the membrane is impervious to the electrolyte solution 48 and to the surrounding liquid medium (not shown), but will permit dissolved oxygen (not shown) to diffuse from the liquid medium into the electrolyte solution 48. The electrolyte solution 48 is protected by the membrane 40 from contamination by the liquid medium (not shown) surrounding the apparatus 20.

The preferred electrolyte solution 48 comprises an aqueous solution including chloride and sulphate salts. An especially preferred electrolyte solution is an aqueous solution comprising 0.1M to 1.5M of either potassium chloride or sodium chloride, and 0.1 to 2M of sodium sulphate. The most preferred electrolyte formulation for use in an apparatus such as that of FIG. 2 includes 1M potassium chloride and 1M sodium sulphate.

During operation, the sensor and reference electrodes 22, 24 are coupled by means of the leads 26, 28 to a monitoring circuit (not shown) including a power supply (not shown). Monitoring circuits for Clark-type sensors, as well as suitable regulated power supplies, are commercially available and well known to those of skill in the art. In an especially preferred embodiment, the leads 26, 28 communicate with the monitoring circuit through the male or female half of a plug-and-socket coupling. The power supply biases the sensor and reference electrodes 22, 24 so that a current flows across the electrolyte solution 48 from the sensor electrode 22 to the reference electrode 24 when oxygen is present in the analyte sample. That is, the sensor electrode 22 is configured as a cathode and the reference electrode 24 is configured as an anode. The preferred voltage imparted across the electrode is −0.8V with the preferred current flow across the electrolyte solution 48 during measurement of 21% $O_2$ being approximately 12 μA.

When the apparatus 20 is exposed to a liquid medium (not shown) including dissolved oxygen (not shown), the oxygen diffuses through the membrane 40 and into the electrolyte solution 48 at a rate proportional to the oxygen partial pressure in the liquid medium. The diffused oxygen migrates toward the sensor electrode 22 and is reduced in accordance with equation (I). This reaction draws electrons from the sensor electrode 22, thereby generating a detectable current. Meanwhile, silver derived from the reference electrode 24 is oxidized by reaction with nearby chloride ions (II).

The sensor and reference signals are conducted through the leads 26, 28 to the monitoring circuit (not shown) which may for example include a galvonometer for measuring current. The measured current is calibrated against current obtained with a known oxygen content sample in order to measure the oxygen content of the analyte sample.

FIG. 3 is a schematic view of a second embodiment 60 of a gas detection apparatus capable of use as a polarographic dissolved oxygen sensor. Unlike the apparatus 20, the apparatus 60 includes a minigrid 62 serving as a sensor electrode that is surrounded by a reference electrode 64. The minigrid 62 intersects a working surface 66 of the apparatus 60 to form an array of sensor microelectrodes 98 distributed along the circumference of a circle on the working surface 66. The diameters of the microelectrodes are on the order of 10 μm. The minigrid 62 preferably consists of woven fibers of an electrically conductive metal such as gold, copper or nickel having regularly spaced vertical and horizontal filaments. It is most preferred to use gold. The reference electrode 64 preferably consists of a cylindrical silver/silver chloride sleeve. A first lead 70 communicates with the minigrid 62 and a second lead 72 communicates with the reference electrode 64.

The minigrid 62 is wrapped around an epoxy core 80 and is surrounded by an electrically insulating epoxy spacer 82. The reference electrode 64 is surrounded by a cylindrical epoxy casing or sleeve 84 which electrically isolates the reference electrode 64 from the surrounding liquid medium (not shown).

A semi-permeable membrane 90 such as Teflon®, polytetrafluoroethylene, covers the working surface 66 of the apparatus 60 and is secured along its periphery in a groove 92 in the casing 84 by means of an elastic ring 94. The casing 84 and the membrane 90 together act as an enclosure for the minigrid 62 and the reference electrode 64, defining a cavity 96 to which the indicating microelectrode array 68 and the reference electrode 64 are exposed. An electrolyte solution 98 is enclosed in the cavity 96 in contact with the indicating microelectrode array 68 and the reference electrode 64. The construction of the minigrid electrode array is detailed in U.S. Pat. No. 5,254,235, the disclosure of which is incorporated by reference.

Figure 1:
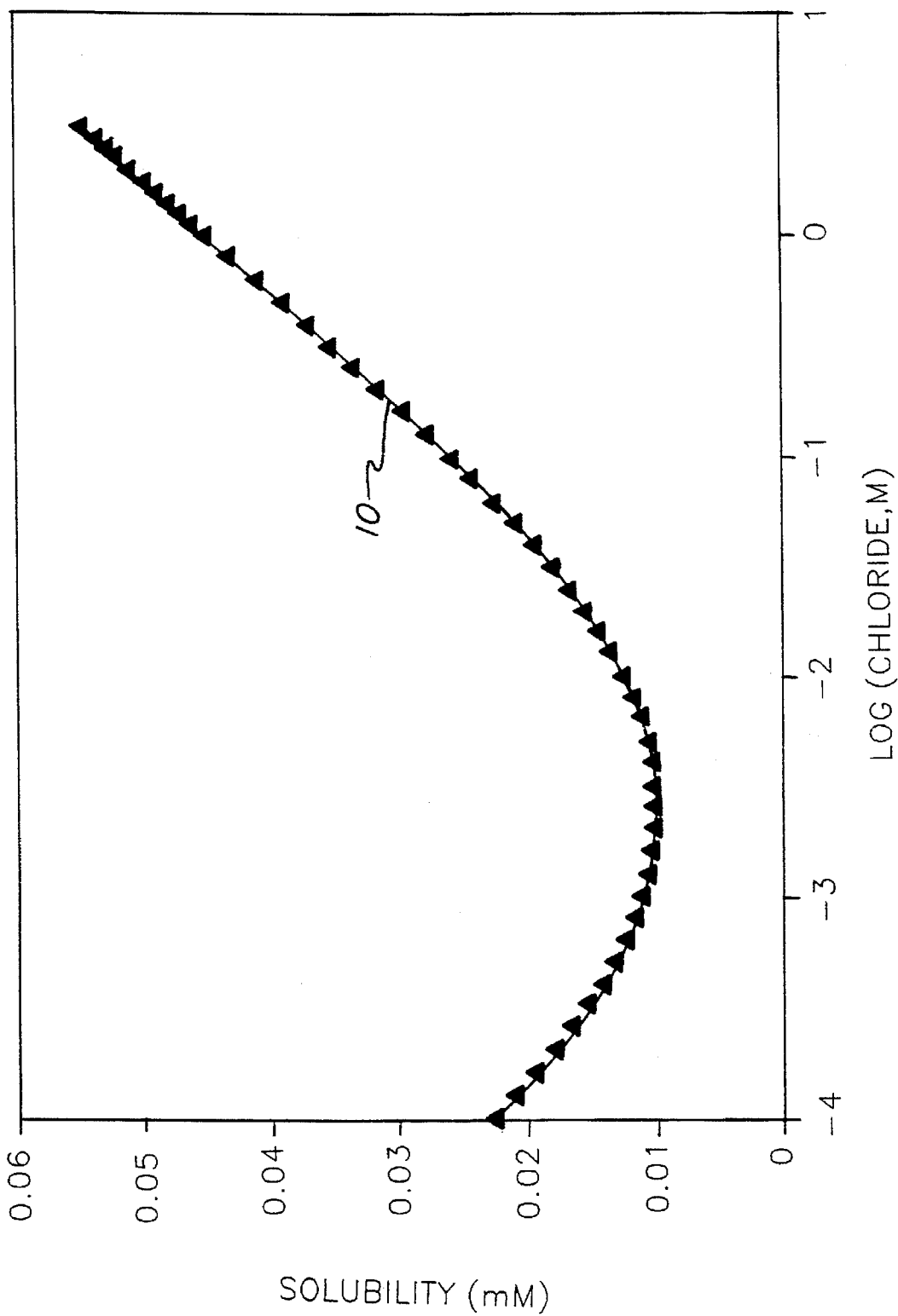
FIG. 1 is a diagram of the solubility of silver chloride in an aqueous chloride solution as a function of chloride ion concentration.

The preferred electrolyte solution 98 for the apparatus 60 of FIG. 3 comprises an aqueous solution including chloride and sulphate salts. An especially preferred electrolyte solution is an aqueous solution comprising approximately 1 mM to 100 mM of either potassium chloride or sodium chloride, and approximately 10 mM to 200 mM of sodium sulphate. The most preferred electrolyte formulation for use in an apparatus such as that of FIG. 3 includes 10 mM sodium chloride and 100 mM sodium sulphate. Referring to FIG. 1, the preferred composition for the electrolyte solution 98 is particularly advantageous in that the solubility of silver chloride is at a local minimum when the chloride ion concentration is on the order of 1–10 mM.

During operation, the minigrid 62 and the reference electrode 64 are coupled by means of the leads 68, 70 to an monitoring circuit (not shown) including a power supply (not shown). Monitoring circuits for Clark-type sensors, as well as suitable regulated power supplies, are commercially available and well known to those of skill in the art. The power supply biases the minigrid 62 and the reference electrode 64 so that when oxygen is present in the analyte sample, a current flows across the electrolyte solution 98 from the sensor microelectrode array 68 to the reference electrode 64. That is, the microelectrodes of the indicating microelectrode array 68 are configured as cathodes and the reference electrode 64 is configured as an anode.

The apparatus 60 (FIG. 3) measures dissolved oxygen concentration in the liquid medium (not shown) by the same operational methods stated above for the apparatus 20 (FIG. 2). Significantly, however, the diameters of the microelectrodes of the indicating microelectrode array 68 (FIG. 3) of the apparatus 60 (FIG. 3) are several orders of magnitude smaller than the diameter of the indicating macroelectrode 22 (FIG. 2) of the apparatus 20 (FIG. 2). As a consequence, the electrical behavior of the apparatus 60 (FIG. 3) is more sensitive to silver deposition than is the electrical behavior of the apparatus 20 (FIG. 2), since the growth of even small dendrites on the minigrid array 62 (FIG. 3) will have a proportionally greater effect on the effective sizes of the microelectrodes 68 (FIG. 3) of the apparatus 60 (FIG. 3) than on the effective size of the macroelectrode 22 (FIG. 2) of the apparatus 20 (FIG. 2). Likewise, the preferred current level in an apparatus of the geometry of the apparatus 60 (FIG. 3) having 100 microelectrodes 68, on the order of 100 nA, is several orders of magnitude less than the preferred current level in apparatus 20 (FIG. 2). In fact, in oxygen sensors of the type shown in FIG. 3, the desired potential impressed across the electrodes is 1.0V with a current of 100 nanoamperes (+/−30) obtained for a 21% oxygen calibration standard. It is for these reasons that the preferred chloride and sulphate salt concentrations in the electrolyte solution 98 (FIG. 3) for use with the apparatus 60 (FIG. 3) are several orders of magnitude less than the preferred chloride and sulphate salt concentrations in the electrolyte solution 48 (FIG. 2) for use with the apparatus 20 (FIG. 2).

While the invention has been described in terms of particular electrode geometries, the electrode geometry is not critical to the invention and other configurations than those shown may be used in conjunction with the disclosed invention. Furthermore, the composition of the sensor electrode 22 or the minigrid 62 is not critical to the invention. While the electrolyte solution has been described as a combination of chloride and sulphate salts, effective amounts of other co-electrolytes may be used in combination with chloride salts if compatible with the other species in the Clark-type sensor.

The invention will be further explained in conjunction with the following examples which are included as being illustrative of the invention and should not be construed to limit the scope of the invention.

EXAMPLE 1

Four YSI 5905 polarographic oxygen sensors (available from YSI Incorporated of Yellow Springs, Ohio) were exposed to air (approximately 21% $O_2$). The sensors had an electrode geometry similar to that shown in FIG. 2, including a gold indicating sensor electrode 22 surrounded by a silver/silver chloride reference electrode 24. An aqueous electrolyte solution including 2.35M potassium chloride is typically used in YSI 5905 sensors.

Different electrolyte formulations were used in each of the four sensors and current levels between the sensor and reference electrodes were measured as functions of applied voltage to compare the performances of the different electrolyte solutions. The electrolyte formulations in each of the four sensors A, B, C and D were as follows:

| Sensor | KCl Concentration | $Na_2SO_4$ Concentration |
| --- | --- | --- |
| A | 2.35M | — |
| B | 0.5M | — |
| C | 0.5M | 1M |
| D | 1M | 1M |

FIG. 4 is a plot of the current conducted across the sensors A, B, C and D as a function of voltage applied between the sensor electrode and the reference electrode. The curves 110, 112, 114 and 116, representing voltammograms for the sensors A, B, C and D, are substantially similar in shape, each including a portion in which the current flow is an approximately linearly increasing function of voltage, followed by a section in which the current is approximately constant at a reduction plateau despite increasing voltage.

The curves 110 and 112 represent voltammograms for the sensors A and B, which used electrolyte solutions comprising 2.35M KCl and 0.5M KCl, respectively. At the portion of the graph depicting rapid increase in current, curve 112 is shifted to the right, toward a more negative potential, relative to curve 110, indicating that a slightly greater voltage difference [E] was required across the electrodes of sensor B (0.5M KCl) than was required across the electrodes of sensor A (2.35M KCl) to induce the same level of current. Without wishing to be bound by any theory of operation, it is believed that two factors contributed to this shift. Since the electrolyte solution used with sensor B had a lower concentration of chloride ions than the electrolyte solution used with sensor A, it had a higher ohmic resistance to current flow than did sensor A. Furthermore, the oxidation potential of the reference electrode became more positive relative to the reduction potential of the reaction occurring near the sensor electrode due to the decrease in chloride ion concentration.

The curve 114 represents the voltammogram for sensor C, which used an electrolyte solution comprising 0.5M KCl+ 1M $Na_2SO_4$. Curve 114 is shifted to the right relative to curve 110, representing sensor A which used an electrolyte solution comprising 2.35M KCl, but is shifted to the left relative to curve 112, representing sensor B which used an electrolyte solution comprising 0.5M KCl. Due to the addition of 1M $Na_2SO_4$, the electrolyte solution used with sensor C had a lower ohmic resistance than the electrolyte solution used with sensor B.

The curve 116 represents the voltammogram for sensor D, which used an electrolyte solution comprising 1M KCl+1M $Na_2SO_4$. Curve 116 is shifted to the left relative to curve 114, representing sensor C, but is nearly coincident with the linearly increasing section of the curve 110, representing the voltammogram for sensor A which used the standard chloride-based electrolyte solution. This similarity in the electrical responses between lines 110, 112 on one hand with 114, 116 on the other suggests that the preferred electrolyte solution could be substituted into currently available Clark-type sensors without redesigning the sensors and the monitoring circuits to accommodate different voltage and current levels. Stated differently, the electrolyte mixtures C, and D resulted in a substantially linear plateau current when the Clark oxygen sensor was operated at applied voltages of about −0.6 and greater (e.g. [E]≧0.6V). Since the commercially available Clark sensors of the type shown in FIG. 2 operate with a Ag/AgCl reference electrode at applied voltages of about −0.8V, the $SO_4^{-2}$ containing electrolytes can be successfully employed in these sensors.

EXAMPLE 2

Sensors A, B, C and D, using the same electrolyte solutions, were next exposed to pure oxygen gas. The voltammograms for the four sensors, shown in FIG. 5, had roughly the same shape as those shown in FIG. 4 for exposure to air. Due to the higher oxygen content for pure oxygen gas than for air, the reduction plateaus for each of the four sensors in FIG. 5 are higher than those in FIG. 4.

Curve 122, representing sensor B which used an electrolyte solution comprising 0.5M KCl, is shifted to the right, toward a more negative potential, relative to curve 120, representing sensor A which used the standard 2.35M KCl electrolyte solution. The net shift between the reduction plateaus of curves 120 and 122 was approximately 180 mV, which was larger than the shift in the presence of air. Without wishing to be bound by any theory of operation, it is believed that the shift of curve 122 relative to curve 120 is greater than the shift of curve 112 (FIG. 4) relative to curve 110 (FIG. 4) because the voltage reduction across the electrolyte solution due to ohmic resistance is greater for the higher current levels observed when the sensors were exposed to pure oxygen gas.

The curve 124, representing the voltammogram for sensor C which used an electrolyte solution comprising 0.5M KCl+1M $Na_2SO_4$, is shifted to the left relative to curve 122, representing sensor B which used an electrolyte solution comprising 0.5M KCl. The net shift between the reduction plateaus of curves 122 and 124 was approximately 100 mV. Once again, it is believed that this shift is primarily attributable to the increase in ionic conductivity in sensor C due to the addition of 1M $Na_2SO_4$ to the electrolyte solution.

The curve 126, representing the voltammogram for sensor D which used an electrolyte solution including 1M KCl+1M $Na_2SO_4$, is shifted slightly to the left relative to curve 114, representing sensor C, toward curve 120, representing sensor A. Unlike the curves 110, 116 (FIG. 4) representing voltammograms for sensors A and D in exposure to air, curves 120 and 124 are not nearly coincident. It is believed that the difference between the reduction plateaus for sensors A and D, approximately 50 mV, is attributable to a lower reference potential in sensor D as compared with sensor A due to lower chloride ion concentration in the electrolyte solution of sensor D. Nonetheless, the electrical responses of sensors A and D are sufficiently similar to indicate that the preferred electrolyte solution of the invention can be substituted for the standard chloride-based electrolyte solution without redesigning the sensors and the monitoring circuits to accommodate different voltage and current levels. Again, use of the sulfate based electrolytes provide a substantially linear current plateau when the sensor is operated at voltages [E] of greater than about 0.6V.

EXAMPLE 3

Four YSI 5905 polarographic oxygen sensors were exposed to an atmosphere of 100% water-saturated air for 8–9 hours per day. For the first 13 days of operation, two of the sensors used the standard 2.35M KCl electrolyte solution while the other two sensors used an electrolyte solution comprising 1M KCl+1M $Na_2SO_4$. The steady-state current of each sensor was measured at the end of each day. Normalized current deviations were determined by taking the difference between the calibration current levels (12 µA+/–2 µA normalized to 100%) (after temperature compensation) for each sensor and the steady state normalized current level measured at the end of the day. Percent current drifts were calculated by dividing the current deviations by the number of hours which had passed since the sensors were calibrated.

The daily percent current drifts as functions of elapsed days for each of the sensors are shown in FIG. 6. Curves 130 and 132 represent the percent drifts for the two sensors originally using the standard 2.35M KCl electrolyte solution, while curves 134 and 136 represent the percent drifts for the two sensors using the 1M KCl+1M $Na_2SO_4$ electrolyte solution. For the first 5 days, each of the four sensors exhibited similar daily percentage drifts, which are believed to be due mainly to the variation of the atmospheric pressure and the water vapor condensation at the membranes of the sensors.

After approximately 6 days of operation, however, one of the sensors using the 2.35M KCl electrolyte solution (curve 130) began to show a significant build-up of silver deposits at the edge of the indicating electrode. In the following days, the daily drifts gradually increased from approximately 0.2%/hr to 0.5%/hr. After approximately 10 days of operation, the other sensor using the 2.35M KCl electrolyte solution (curve 132) began to show even more significant build-up of silver deposits. Its drift rate increased to approximately 0.8%/hr. The two sensors using the 1M KCl+1M $Na_2SO_4$ electrolyte solution (curves 134 and 136) showed no sign of dendrite growth and continued to show only modest daily percentage drifts attributable to condensation on their membranes and variations of atmospheric pressure.

After approximately 13 days, the 2.35M KCl electrolyte solutions in the first two sensors were replaced by 1M KCl+1M $Na_2SO_4$ solutions. No further dendrite formation was observed in any of the four sensors during the following 33 days, and all four sensors showed similar modest variations.

As these examples demonstrate, polarographic sensors using silver/silver chloride reference electrodes and electrolyte solutions including sulphate and chloride salts in accordance with the invention have unexpectedly lower silver deposition rates on their sensor electrodes than do sensors using conventional chloride-based electrolyte solutions, without sacrificing the current levels required to carry out polarographic measurements.

Accordingly, combinations of sulphate and chloride containing electrolytes may be used in polarographic cells of the type having Ag/AgCl reference electrodes disposed therein in order to inhibit Ag dendrite formation or deposit on the cathode. Surprisingly, these combined electrolyte solutions still result in substantially linear current plateaus when voltages [E] of greater than about 0.6, preferably about 0.6–1.2V, are applied across the electrodes. This effect is significant since conventionally available Clark type sensors such as those depicted in FIGS. 2 and 3, do not need physical modification or retrofitting in order to take advantage of this dendrite inhibition property. Instead, the combined $SO_4^{-2}$/$Cl^{-1}$ electrolytes can be simply substituted for the total $Cl^{-1}$ electrolytes presently used.

As indicated above, the commercially available Clark oxygen sensors of the type depicted in FIG. 2 are usually set to operate at –0.8V with the commercially available minigrid assemblies set to operate at –1.0V. Since the combined $SO_4^{-2}$/$Cl^{-1}$ electrolytes produce substantially linear (or flat) plateau like currents at those voltages, reliable oxygen measurements can be made when these electrolytes are substituted for the now used NaCl or KCl electrolytes.

The molar ratio of $Cl^-$:$SO_4^{-2}$ ions to be provided in the combined electrolyte that may be used in the invention varies over a wide range of from about 0.005–15 moles $Cl^-$:0.066–200 moles $SO_4^{-2}$ depending on the size of the cathode used. In those instances in which a Clark sensor such as that shown in FIG. 2 is utilized, a molar ratio of about 0.05–15 moles $Cl^-$:0.66–20 moles $SO_4^{-2}$ is exemplary. In such cases a molar ratio of about 1:1 is preferred.

When the mini-grid type of sensor shown in FIG. 3 is used, a molar ratio of about 0.005–10 moles $Cl^-$:0.1–200 moles $SO_4^{-2}$ is exemplary with a molar ratio of 0.1:1 being preferred.

It is apparent that, in its broad aspects, the invention pertains to substitution of $SO_4^{-2}$ ions for $Cl^{-1}$ ions, the latter of which are conventionally incorporated as an anion source in the electrolyte solution incorporated in a Clark type polarographic cell having a gold sensor electrode and a Ag/AgCl anode/reference electrode. This substitution (or use of $SO_4^{-2}$ containing electrolytes in lieu of or in combination with $Cl^{-1}$ electrolytes) inhibits Ag based dendrite formation on the sensor electrode or cathode without deleteriously affecting the current produced when such systems are operated at voltages [E] of greater than about 0.6V for conventional Clark electrodes of the type shown in U.S. Pat. NO. 2,913,386 and [E] about 0.8V for microelectrode arrays such as those shown in U.S. Pat. No. 5,254,235.

Although the invention has been specifically described in conjunction with a Au sensor electrode —Ag/AgCl reference electrode polarographic system such as the types disclosed in the aforementioned U.S. Pat. Nos. 2,913,386 and 5,254,235, it is to be noted that the invention is also applicable when other types of sensor electrodes such as Pt, Cu, Ni or other metals are used in a chloride containing electrolyte in conjunction with a silver or silver—silver chloride reference electrode. Of course in these systems the [E] required to obtain a substantially linear current on a polarogram will vary from those shown in the above examples and description.

Various changes or modifications in the invention described may occur to those skilled in the art without departing from the true spirit or scope of the invention. The above description of preferred embodiments of the invention is intended to be illustrative and not limiting, and it is not intended that the invention be restricted thereto but that it be limited only by the true spirit and scope of the appended claims.

What is claimed is:

1. Apparatus for detecting a gas dissolved in a liquid medium comprising:

an aqueous electrolyte solution;

an enclosure defining a cavity for containing the aqueous electrolyte solution, the enclosure being permeable to the gas and substantially impermeable to the liquid medium; and a plurality of spaced electrodes in electrical communication with the aqueous electrolyte solution, said electrodes comprising a reference electrode and a sensor electrode;

wherein said reference electrode of the plurality of spaced electrodes includes a material selected from the group consisting of silver, silver chloride and alloys thereof, and the aqueous electrolyte solution includes approximately 1 mM to 1.5M of a chloride salt and 10 mM to 2M of a sulphate salt.

2. The apparatus as recited in claim 1 wherein the aqueous electrolyte solution includes approximately 0.1M to 1.5M of the chloride salt and approximately 0.1M to 2M of the sulphate salt.

3. The apparatus as recited in claim 1 wherein the aqueous electrolyte solution includes approximately 1 mM to 100 mM of the chloride salt and approximately 10 mM to 200 mM of the sulphate salt.

4. The apparatus as recited in claim 1 wherein the chloride salt is selected from the group consisting of potassium chloride and sodium chloride.

5. In a polarographic cell of the type having a sensor electrode, an Ag containing reference electrode, conductor means electrically connecting said sensor electrode and said reference electrode, and wherein a voltage potential having an absolute value of about 0.6V or greater is impressed across said electrodes, a method for inhibiting formation of Ag dendrites on said sensor electrode comprising providing an aqueous electrolyte solution in said cell having chloride and sulphate ions therein.

6. Method as recited in claim 5 wherein said electrolyte solution comprises a molar ratio of chloride:sulfate ions of between about 0.005–15:0.066–200.

7. Method as recited in claim 6 wherein said electrolyte comprises a molar ratio of chloride:sulfate ions of between about 0.005–10:0.1–200.

8. Method as recited in claim 7 wherein said molar ratio is about 0.1:1.

9. In a method of determining oxygen content of an analyte sample in a polarographic sensor having a sensor electrode, a reference electrode comprising silver, silver chloride or mixtures of silver and silver chloride, conductor means electrically connecting said sensor electrode and said reference electrode, and means for imparting a voltage potential having an absolute value of about 0.6V or greater across said electrodes, a method for inhibiting the formation of Ag based deposits on said sensor electrode comprising providing an aqueous electrolyte solution having $Cl^{-1}$ and $SO_4^{-2}$ ions therein, the molar ratio of said $Cl^{-1}:SO_4^{-2}$ ions being between about 0.005–15:0.066–200.

10. In a method of determining oxygen content of an analyte sample in a polarographic sensor having a sensor electrode, a reference electrode comprising silver, silver chloride, or mixtures of silver and silver chloride, conductor means electrically connecting said sensor electrode and said reference electrode, and means for imparting a voltage potential across said electrodes, a method for inhibiting the formation of Ag based deposits on said sensor electrode comprising providing an aqueous electrolyte solution having $Cl^{-1}$ and $SO_4^{-2}$ ions therein.

11. Method as recited in claim 10 further comprising providing a Pt sensor electrode.

12. Aqueous electrolyte formulation in combination with a polarographic cell gas sensor comprising an Ag containing reference electrode, said electrolyte formulation comprising an aqueous mixture including dissociable chloride and sulfate salts, the molar ratio of chloride:sulfate salts being about 0.005–15:0.066–200.

13. Apparatus for detecting a gas dissolved in a liquid medium comprising:

an aqueous electrolyte solution;

an enclosure defining a cavity for containing the aqueous electrolyte solution, the enclosure being permeable to the gas and substantially impermeable to the liquid medium; and a plurality of spaced electrodes in electrical communication with the aqueous electrolyte solution, said electrodes comprising a reference electrode and a sensor electrode;

wherein said reference electrode of the plurality of spaced electrodes includes a material selected from the group consisting of silver, silver chloride and alloys thereof, and the aqueous electrolyte solution includes approximately 1 mM to 1.5M of a chloride salt and 10 mM to 2M of a sulphate salt, wherein said sulphate salt comprises a member selected from the group consisting of potassium sulphate and sodium sulphate.

14. In a polarographic cell of the type having a sensor electrode, an Ag containing reference electrode, conductor means electrically connecting said sensor electrode and said reference electrode, and wherein a voltage potential having an absolute value of about 0.6V or greater is impressed across said electrodes, a method for inhibiting formation of Ag dendrites on said sensor electrode comprising providing an aqueous electrolyte solution in said cell having chloride and sulphate ions therein wherein the molar ratio of chloride ions to sulfate ions in said electrolyte solution is between about 0.05–15 moles of chloride ions to about 0.066–20 moles of sulfate ions.

15. Method as recited in claim 14 wherein the molar ratio of chloride ions to sulfate ions is about 1:1.

16. In a method of determining oxygen content of an analyte sample in a polarographic sensor having a sensor electrode, a reference electrode comprising silver, silver chloride or mixtures of silver and silver chloride, conductor means electrically connecting said sensor electrode and said reference electrode, and means for imparting a voltage potential having an absolute value of about 0.6V or greater across said electrodes, a method for inhibiting the formation of Ag based deposits on said sensor electrode comprising providing an aqueous electrolyte solution having $Cl^{-1}$ and $SO_4^{-2}$ ions therein, the molar ratio of said $Cl^{-1}:SO_4^{-2}$ ions being between about 0.005–15:0.066–200, and providing an Au sensor electrode.

17. Method as recited in claim 16 wherein the molarity of said aqueous electrolyte solution is at least 1.

18. Method as recited in claim 17 wherein said method comprises imparting a voltage potential having an absolute value of about 0.8V across said electrodes and providing an aqueous electrolyte solution having a molar ratio of $Cl^{-1}:SO_4^{-2}$ ions of between about 0.05–15:0.66–20.

19. Method as recited in claim 18 wherein said method comprises providing an aqueous electrolyte solution having a molar ratio of $Cl^{-1}:SO_4^{-2}$ ions of about 1:1 and wherein the molarity of said electrolyte is about 2.0.

20. Method as recited in claim 16 wherein said reference electrode comprises a mini-grid array of microelectrodes, said method comprising imparting a voltage potential having an absolute value of about 1.0V across said sensor electrode and said reference electrode and providing an aqueous electrolyte solution having a molar ratio of about 0.005–10 $Cl^{-1}:0.1–200\ SO_4^{-2}$ ions.

21. Method as recited in claim 20 wherein said molar ratio is about 0.1:1.

* * * * *